United States Patent
Khanuja et al.

(10) Patent No.: US 6,833,249 B2
(45) Date of Patent: Dec. 21, 2004

(54) QUICK AND SENSITIVE METHOD OF QUANTIFYING MYCOLIC ACID TO DEVELOP ANTI-MICROBIAL AGENTS AND A DIAGNOSTIC KIT THEREOF

(75) Inventors: Suman Preet Singh Khanuja, Uttar Pradesh (IN); Suchi Srivastava, Uttar Pradesh (IN); Tiruppadiripuliyur Ranganathan Santha Kumar, Uttar Pradesh (IN); Ajit Kumar Shasany, Uttar Pradesh (IN)

(73) Assignee: Council of Scientific and Industrial Research (IN)

( * ) Notice: Subject to any disclaimer, the term of this patent is extended or adjusted under 35 U.S.C. 154(b) by 216 days.

(21) Appl. No.: 10/102,939

(22) Filed: Mar. 22, 2002

(65) Prior Publication Data

US 2003/0180708 A1 Sep. 25, 2003

(51) Int. Cl.$^7$ .............. C12Q 1/18; C12Q 1/02; G01N 33/53
(52) U.S. Cl. ............ 435/32; 435/29; 435/136; 435/253.1; 435/975; 436/71; 532/1
(58) Field of Search ............ 435/32, 29, 136, 435/253.1, 975; 532/1; 436/71

(56) References Cited

U.S. PATENT DOCUMENTS 5,219,890 A * 6/1993 Boucher ............... 514/705

OTHER PUBLICATIONS

Blank et al. "A Method for the Quantitative Determination of Glycerolipids Containing o–Alkyl and o–alk–1–enyl Moieties" Biochim. Biophys. Acta (1975) 380(2): 208–218.*

Michalec et al. "Qualitative and Quantitative Thin–Layer Chromatography of Mycolic Acids in *Mycobacterium tuberculosis* var. bovis–BCG" J. Chromatog. (1975) 104: 460–464.*

Garza–Gonzalez et al. "Determination of Drug Susceptibility of *Mycobacterium tuberculosis* Through Mycolic Acid Analysis" J. Clin. Microbiol. (May 1997) 35(5): 1287–9.*

* cited by examiner

*Primary Examiner*—Jean C. Witz
*Assistant Examiner*—Susan Hanley
(74) *Attorney, Agent, or Firm*—Dickinson Wright PLLC

(57) ABSTRACT

The present invention relates to a rapid, sensitive, simple, and cost-effective spectrophotometric method of detecting and quantifying mycolic acid in a mycolic acid-fuschin dye complex with absorbance maxima ranging between 490–500 nm in the presence of various test compounds, for screening mycolic acid biosynthesis inhibitors useful as anti-microbial agents and a diagnostic kit thereof comprising basic fuschin dye in the concentration ranging between 0.1–1.0 gm/100 ml, phenol and 95% ethanol in the ratio ranging between 1:4 to 2:1 (v/v), and phenol and distilled water in the ratio ranging between 1:14 to 1:25.

12 Claims, 4 Drawing Sheets

Figure 1: Spectral scan of mycolic acid (5 µg /ml) in hexane
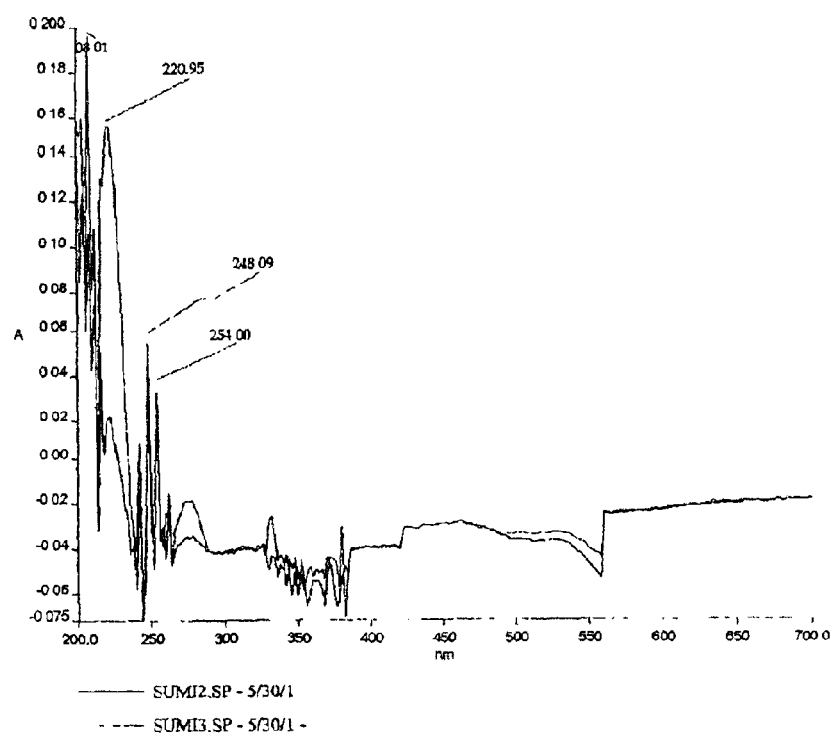

Figure 2: spectral scan of Carbol-fuschin dye
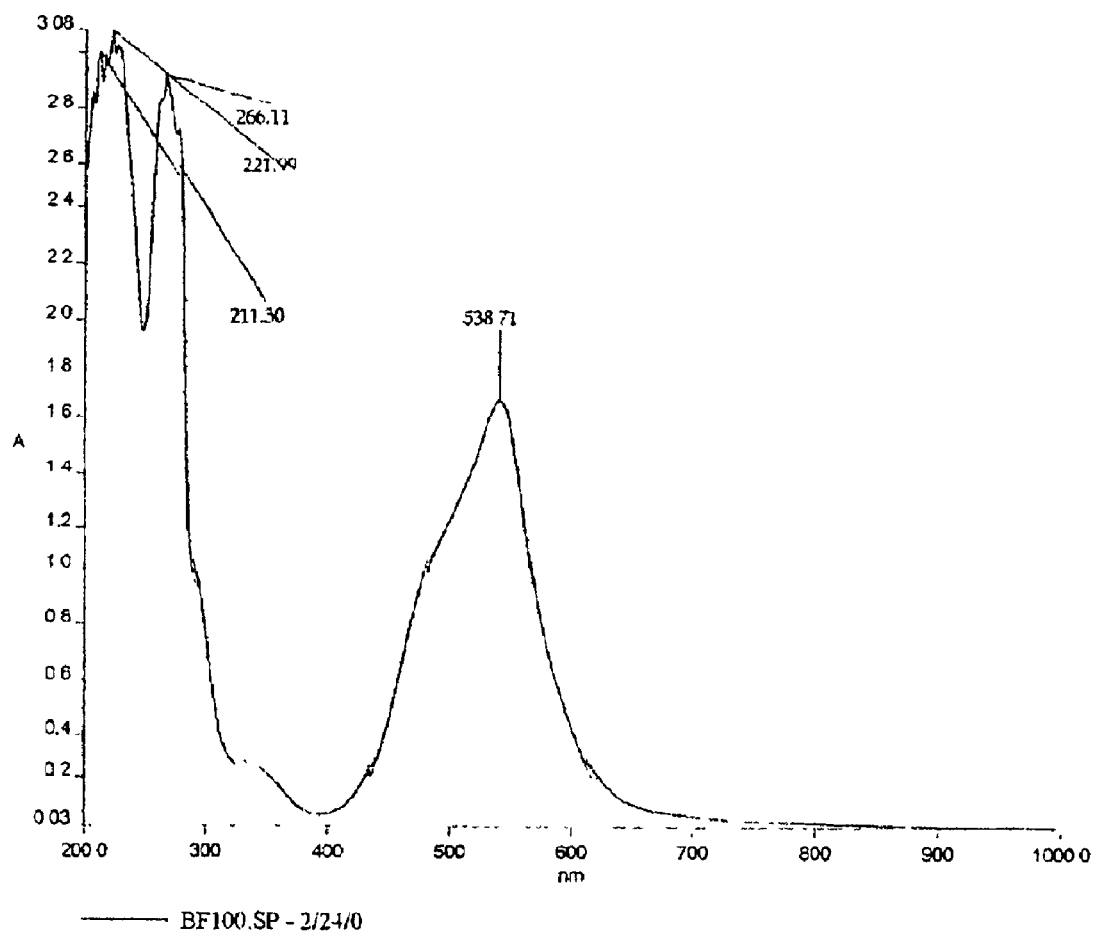

Figure 3: Spectral scan of mycolic acid (5 µg /ml) - carbol fuschin complex in hexane
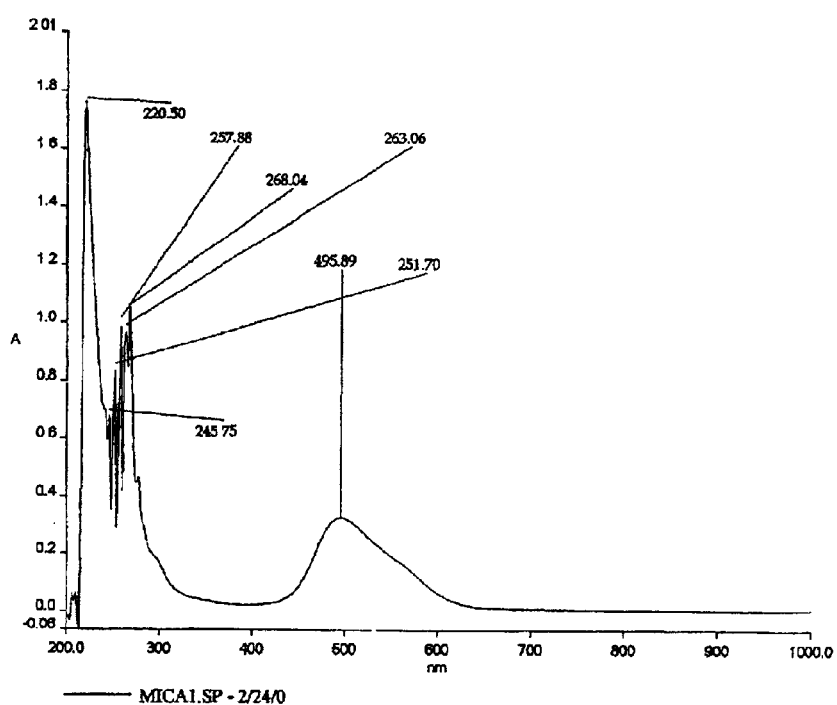

Figure 4: Increase in absorbance with increase concentration of mycolic acid when complexed with carbol fuschin dye
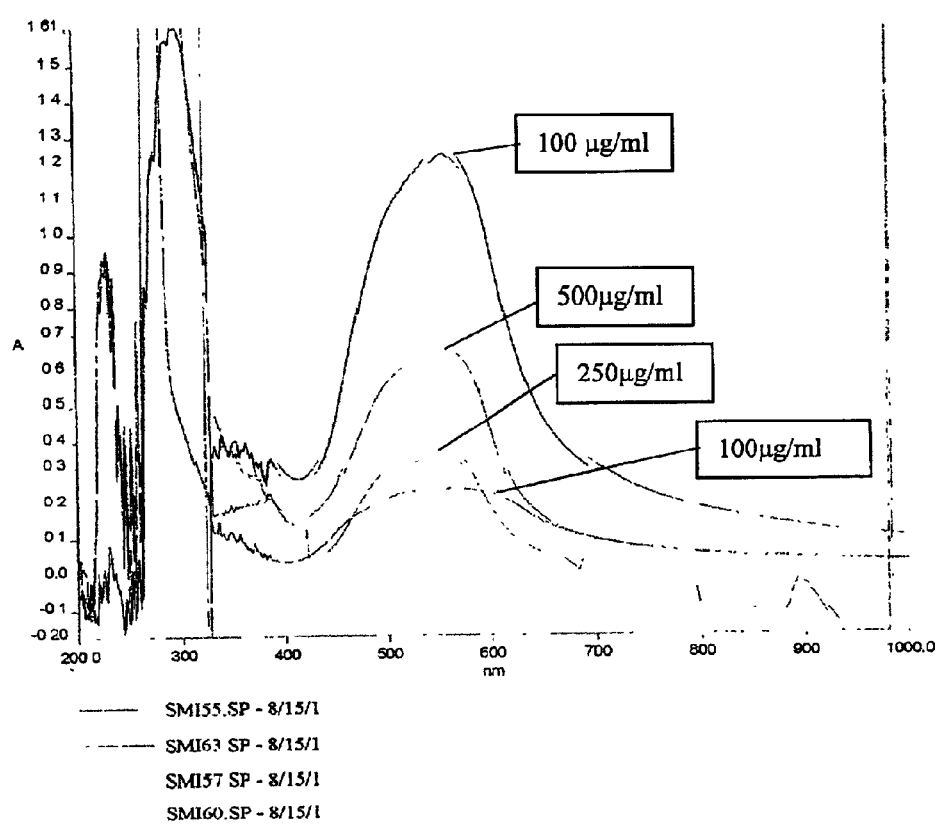

QUICK AND SENSITIVE METHOD OF QUANTIFYING MYCOLIC ACID TO DEVELOP ANTI-MICROBIAL AGENTS AND A DIAGNOSTIC KIT THEREOF

FIELD OF THE INVENTION

The present invention relates to a rapid, sensitive, simple, and cost-effective spectrophotometric method of detecting and quantifying mycolic acid in a mycolic acid-fuschin dye complex with absorbance maxima ranging between 490–500 nm in the presence of various test compounds, for screening mycolic acid biosynthesis inhibitors useful as anti-microbial agents and a diagnostic kit thereof comprising basic fuschin dye in the concentration ranging between 0.1–1.0 gm/100 ml, phenol and 95% ethanol in the ratio ranging between 1:4 to 2:1 (v/v), and phenol and distilled water in the ratio ranging between 1:14 to 1:25.

BACKGROUND OF THE INVENTION

Tuberculosis caused by *Mycobacterium tuberculosis* is a public health problem, which has increased in importance during the last two decades, due in part to the increasing number of cases caused by the association of acquired immunodeficiency syndrome (AIDS) and the appearance of multiple drug-resistant strains. Other mycobacteria which are often indistinguishable from tuberculosis have also increased.

The current method of detection is by determining the mycolic acid patterns from clinical isolates of sputum, cerebrospinal fluid, bronchial washing, corneal ulcer, and bone marrow, as well as from acid-fast stain smear-positive clinical specimens. Standardized mycolic acid extraction methods are used to ensure the maximal extraction of mycolic acid derivatives to enhance the sensitivity of the method. Different chromatographic columns are used to identify the species of mycolic acid. The immediate detection of bacteria containing mycolic acid is through acid fast staining and detection through the microscope. Lipid-rich cell walls are not permeable by ordinary stains.

The stain consisting of a basic dye (fuchsin) and phenol (a lipid solvent) is used for the purpose. Phenol partially solubilizes the cell wall and allows fuchsin to penetrate the wall and bind to mycolic acid.

After fuchsin is incorporated, it is resistant to decolorization even after exposure to acid alcohol, a property that characterizes mycobacteria and that can be performed on unprocessed clinical specimens, concentrated specimens, or cultures.

This principle is widely used to identify bacteria producing mycolic acid with the help of a microscope. But an improved system based on visual detection of the mycolic acid is the need of the hour to screen out potential mycolic acid biosynthesis inhibiting compounds from a vast array of plant compounds.

The detection and quantification procedure can be made more accurate by using the help of spectrophotometer. The amount of inhibition can be quantified simply through optical density measurement at a particular wavelength. This does not necessitate the complex, high cost technologies like IR, NMR, GC spectroscopy for the detection, which are currently being used.

The amount of mycolic acid which cannot be quantified through acid fast staining followed by microscopic detection can be quantified by systematic extraction and dye binding followed by spectrophotometric analysis. Keeping this in mind, a simple, rapid, cost effective procedure kit was devised to detect and quantify the mycolic acid which in turn resulted in a high efficiency screen to identify potential inhibitors of mycolic acid biosynthesis.

The protocols for extraction, isolation of mycolic acid and detection of bacteria-producing mycolic acid through acid fast staining are known in the art. But the system as a whole is inefficient and requires a microscope to detect the presence of the bacteria-producing mycolic acid.

Similarly, extraction, isolation and characterization of mycolic acid is carried out through different methods of chromatography and IR, NMR spectroscopy. The emphasis of the present invention was to generate a system to screen a large amount of plant extracts and compounds with potential mycolic acid biosynthesis inhibiting activity, rapidly and with a low cost.

OBJECTS OF THE INVENTION

The main object of the present invention is to develop a quick, simple, sensitive, cost-effective method of identifying mycolic acid.

Another main object of the present invention is to develop a quick, simple, sensitive, cost-effective method of quantifying mycolic acid.

A further object of the present invention is to develop a quick, simple, sensitive, cost-effective spectrophotometric method of identifying and quantifying mycolic acid.

Yet another object of the present invention is to use carbol-fuschin dye and mycolic acid complex to develop a quick, simple, sensitive, cost-effective spectrophotometric method of identifying and quantifying mycolic acid.

Still another object of the present invention is to develop a method of screening test compounds for their mycolic acid inhibitory properties.

Still another object of the present invention is to develop a diagnostic kit for the detection of mycolic acid by spectrophotometry.

SUMMARY OF THE INVENTION

The present invention relates to a rapid, sensitive, simple, and cost-effective spectrophotometric method of detecting and quantifying mycolic acid in a mycolic acid-fuschin dye complex with absorbance maxima ranging between 490–500 nm in the presence of various test compounds, for screening mycolic acid biosynthesis inhibitors useful as anti-microbial agents and a diagnostic kit thereof comprising basic fuschin dye in the concentration ranging between 0.1–1.0 gm/100 ml, phenol and 95% ethanol in the ratio ranging between 1:4 to 2:1 (v/v), and phenol and distilled water in the ratio ranging between 1:14 to 1:25.

DETAILED DESCRIPTION OF THE INVENTION

Accordingly, the present invention relates to a rapid, sensitive, simple, and cost-effective spectrophotometric method of detecting and quantifying mycolic acid in a mycolic acid-fuschin dye complex with absorbance maxima ranging between 490–500 nm in the presence of various test compounds, for screening mycolic acid biosynthesis inhibitors useful as anti-microbial agents and a diagnostic kit thereof comprising basic fuschin dye in the concentration ranging between 0.1–1.0 gm/100 ml, phenol and 95% ethanol in the ratio ranging between 1:4 to 2:1 (v/v), and phenol and distilled water in the ratio ranging between 1:14 to 1:25.

According to an embodiment of the present invention there is provided a rapid, simple, sensitive, and cost effective method of screening mycolic acid biosynthesis inhibitors useful as anti-microbial agents by quantifying the amount of mycolic acid produced by bacteria in the presence and absence of test compound or extract.

According to another embodiment of the present invention, there is provided the step growing separate cultures of the specified bacteria in the presence and absence of the specified compound or extract for time duration ranging between 40–60 hours.

According to yet another embodiment of the present invention, a lyophilizing bacterial pellet is produced.

According to still another embodiment of the present invention, there is provided the step of extracting mycolic acid by a conventional method.

According to still another embodiment of the present invention, there is provided the step of dissolving extracted mycolic acid extract in hexane to obtain mycolic acid solution.

According to still another embodiment of the present invention, there is provided the step of adding the specified solution to carbol-fuschin dye in the ratio ranging between 1:4 to 4:1 (v/v).

According to still another embodiment of the present invention, there is provided the step of shaking the product of the above step vigorously to obtain a pink color mycolic acid-dye complex as an upper layer.

According to still another embodiment of the present invention, there is provided the step of quantifying the specified mycolic acid spectrophotometrically at a wavelength ranging between 490–500 nm.

According to still another embodiment of the present invention, there is provided the step of determining the degree of inhibition of mycolic acid biosynthesis in the compound-treated bacterial culture.

In still another embodiment of the present invention, wherein quantifying mycolic acid level spectrophotometrically at wavelength preferably ranging between 494–496 nanometer.

According to still another embodiment of the present invention, the ratio of carbol fuchsin dye to the specified extract is preferably 1:1 (v/v).

According to still another embodiment of the present invention, the carbol fuschin consists of basic fuschin dye in the concentration ranging between 0.1–1.0 gm/100 ml, phenol, 95% ethanol, and distilled water, the constituents being provided in the ratio, phenol:ethanol in ratio ranging between 1:4 to 2:1 (v/v), and phenol: distilled water in the ratio ranging between 1:25 to 1:14 (v/v).

According to still another embodiment of the present invention, the specified test compound or extract with inhibitory activity is added at concentrations ranging between $\frac{1}{25}$ to $\frac{1}{2}$ of minimum inhibitory concentration (MIC).

According to still another embodiment of the present invention, the specified anti-microbial agents are developed against microbes comprising *Mycobacterium, Corynebacterium*, and *Nocardia*.

According to still another embodiment of the present invention, the specified method is used to screen for inhibitors selected from a group comprising synthetic, semi-synthetic, natural compounds, and extracts.

According to still another embodiment of the present invention, the intensity of color increases with an increase in the concentration of mycolic acid.

According to still another embodiment of the present invention, the specified method works for mycolic acid from all sources.

According to a further embodiment of the present invention, a diagnostic kit is provided that is useful for identifying potential anti-microbial drugs against mycolic acid producing microbes, the kit comprising carbol fuschin, methanol, toluene, hexane, concentrated sulphuric acid, a bacterial pellet, and a test compound or extract, with the constituents in the ratio: methanol:toluene ranging between 1:3 to 3:1 (v/v), methanol:hexane ranging between 8:1 to 2:1 (v/v), concentrated sulphuric acid:hexane ranging between 1:8 to 1:2 (v/v), and carbol fuschin:hexane extract ranging between 1:4 to 4:1 (v/v), with methanol, toluene, and concentrated sulphuric acid of above-mentioned ratio added into lyophilized bacterial pellet with final concentration of the same ranging between 0.1–3.0 gm/100 ml.

According to still another embodiment of the present invention, the carbol fuschin consists of basic fuschin dye in the concentration ranging between 0.1–1.0 gm/100 ml, phenol, 95% ethanol, and distilled water, the constituents being provided in the ratio: phenol:ethanol in ratio ranging between 1:4 to 2:1 (v/v), and phenol:distilled water in the ratio ranging between 1:14 to 1:25 (v/v).

According to still another embodiment of the present invention, the specified anti-microbial agents are developed against microbes comprising *Mycobacterium, Corynebacterium*, and *Nocardia*.

According to still another embodiment of the present invention, the specified test compound or extract with inhibitory activity is added at concentrations ranging between $\frac{1}{25}$ to $\frac{1}{2}$ of minimum inhibitory (MIC).

According to another embodiment of the present invention, in acid fast staining, a characteristic feature of the genus Mycobacteria causes mycolic acid to bind with carbol fuchsin dye to give the pink colour of the acid fast bacilli.

According to yet another embodiment of the present invention, on the basis of this principle a spectrophotometric assay procedure was developed, in which the hexane extract of mycolic acid, when kept in a screw cap vial along with carbol fuchsin dye, hexane fraction forms upper colorless layer and the dye forms the lower pink layer, but as the vial is mixed vigorously the carbol fuchsin dye binds to mycolic acid present in the hexane layer and forms an upper pink layer the intensity of which increases and a lower transparent layer in which intensity of pink colour decreases depending on the amount of mycolic acid present in the upper hexane layer.

According to still another embodiment of the present invention, during vigorous mixing of dye with the hexane layer, there is a binding to mycolic acid to form a complex and the amount of dye goes into hexane layer depending upon the concentration of mycolic acid in the hexane layer, whereas normal hexane without mycolic acid does not form the complex to give the characteristic upper pink layer.

According to still another embodiment of the present invention, a method is disclosed for the screening of mycolic acid biosynthesis inhibitors. More particularly the method is used to detect and quantify the relative amount of mycolic acid in a mixture or a solution or a culture leading to the identification of inhibitors of mycolic acid biosynthesis, thus being useful as a screening procedure to detect potential drug compounds for inhibition of mycolic acid biosynthesis. This invention also relates to a detection kit for mycolic acid that can be used as a diagnostic kit. The present invention has direct implication in simplifying the procedure of rapid detection of compounds inhibiting the biosynthesis of mycolic acid and ultimately leading to the production of an antimicrobial drug.

According to still another embodiment of the present invention, the fact that mycolic acids in mycobacteria bind to carbol fuschin is well known. In fact, using this principal, the clinical specimens are routinely tested for the presence of mycobacterium in hospitals and diagnostic labs but with the help of a microscope, which is a laborious procedure. Moreover, the microscope method cannot be used for other applications such as drug screening where quantification of mycolic acid production by mycobacterium is a necessity.

According to still another embodiment of the present invention, the method described herein relies on the same principles but enables the quantification of the mycolic acid production and/or its inhibition in mycobacterium. The instant invention is not provided according to this principle but for the simple rapid, quantitative method for the detection of mycolic acid using a diagnostic kit and technique of spectrophotometry.

According to still another embodiment of the present invention, the present invention facilitates an improved quantification of mycolic acid presence and thus the presence of mycobacterium in any given sample. Also it facilitates an improved quantification of inhibition of mycolic acid synthesis useful in drug screening programs for the identification of mycolic acid inhibitors.

BRIEF DESCRIPTION OF THE ACCOMPANYING DRAWINGS

FIG. 1 shows spectral scan of mycolic acid (5 micrograms/ml) in hexane.

FIG. 2 shows spectral scan of carbol-fuschin dye.

FIG. 3 shows spectral scan of mycolic acid (5-micrograms/ml)-carbol fuschin complex in hexane.

FIG. 4 shows increase in absorbance with the increase in concentration of mycolic acid when complexed with carbol fuschin dye.

The invention of this simple, novel and rapid system to detect potential mycolic acid biosynthesis inhibitors will be illustrated in the following examples which are provided to illustrate the invention and therefore should not be considered to limit the scope of the present invention.

EXAMPLES

Example 1

Mycolic Acid Extraction

Mycolic acids are branched, β-hydroxy fatty acids which occur in the cell wall of *Corynebacterium, Nocardia and Mycobacterium*. Their molecular size varies with the genus, i.e., from 30, 50, 80-carbon atoms in the order described above. Because of the correlation between genus and mycolic acid size, the test for this biochemical marker is done in the early stage of the identification of unknown actinomycetes. The method followed in this invention for the extraction of mycolic acid is according to Minniken et al. (1975). After proper growth of the bacteria, the culture is centrifuged at 5000 RPM for 5 minutes and lyophilized. Dry bacteria (100 mg) are mixed with methanol (5 ml), Toluene (5 ml) and concentrated sulphuric acid (0.2 ml) in a 20-ml screw cap tube (poly tetra fluoro ethylene lined). The contents of the tube are mixed thoroughly and methanolysis is allowed to proceed for 12–16 hours at 75° C. (stationary incubation). The reaction mixture is allowed to cool and mycolic acid is extracted by adding 1 ml of hexane. After vigorous mixing the mixture is allowed to settle and the upper hexane layer containing mycolic acid is collected. Samples of the hexane extract were spotted on TLC coated with Merck silica gel H (0.5 mm), along with standard mycolic acid and the chromatogram is developed in petroleum ether: diethyl ether (85:15). The positions of the separated components were revealed by charring at 150–200° C. after spraying with chromic acid solution (5 gm $K_2Cr_2O_7$, in 5 ml $H_2O$, made up to 100 ml with concentrated H2SO4, then diluted 10 times with water).

Example 2

The spectral scan of pure mycolic acid (procured from Sigma Chemical Co.) was performed from 200 nm to 1000 nm. In the visible range prominent peaks were not detected (FIG. 1).

Example 3

The spectral scan of carbol fuschin (basic fuschin 0.3 g, ethyl alcohol (95%) 10.0 ml, phenol 5.0 ml, distilled water 95 ml) was analyzed from 200 nm to 1000 nm and a distinct peak at 538.71 was recorded in the visible range indicating the colour of the stain (FIG. 2).

Example 4

When mycolic acid in hexane was added to carbol fuschin (1:1 ratio v/v), carbol fuschin formed the lower pink layer and mycolic acid in hexane formed the upper transparent layer. After thorough mixing the upper hexane layer turned pink due to the complex formed between the stain and mycolic acid. Since mycolic acid is soluble in hexane and cannot come to the dense carbol fuschin layer the stain came to the upper hexane layer imparting pink colour to the upper layer. This simple system was exploited further to screen potential inhibitors of mycolic acid biosynthesis. The UV-Visible spectra of the complex of mycolic acid and fuschin in hexane layer was scanned from 200 nm to 1000 nm and found a shift in the peak of stain 538.71 nm to 495.89 nm indicating the formation of a complex with mycolic acid (FIG. 3).

Example 5

To confirm again that mycolic acid is the only candidate responsible for formation of such complex a calorimetric assay of hexane extract from *Bacillus subtilis* and *Escherichia coli* (non-producer of mycolic acid) were used and the observations are described in this example. When only the hexane layer was mixed with carbol fuschin no change in colour was observed. The upper hexane layer remained colorless and the lower dye layer pink, even after vigorous mixing. Similar observations were recorded when the hexane layer contained the extract of *Bacillus subtilis* and *Escherichia coli*. But the pink colour intensity of the lower layer carbol fuschin dye decreased when the hexane layer was having the *Mycobacterium smegmetis* extract and broth with the upper hexane layer turning to pink with vigorous mixing indicating the presence of mycolic acid.

TABLE 1

Colour of carbol fuschin and hexane layers in different treatments

| Contents | Colour of the lower layer | Colour of the Upper layer |
|---|---|---|
| Dye (Carbol Fuchsin) + Hexane | Pink | Colorless |
| Dye (Carbol Fuchsin) + Hexane extract of *Mycobacterium smegmatis* | Reduced intensity of pink colour | Pink |
| Dye (Carbol Fuchin) + Hexane extract of *Bacillus subtilis* | Pink | Colorless |
| Dye (Carbol fuchsin) + Hexane extract of *Escherichia coli* | Pink | Colorless |
| dye (Carbol fuchsin) + Broth Culture of *Mycobacterium smegmatis* | Reduced intensity of pink colour | Pink |

The following strains were used:
1. M. smegmatis MTCC 6 (equivalent to ATCC 14468)= J.Gen.Microbiol. 28: 339 (1962).
2. B. subtilis MTCC 121 (equivalent to ATCC 6051)= Type strain, phage host, blood screening for phenylketonuria.
3. E. coli MTCC 739 (equivalent to ATCC 10536)= Standard antibiotic test strain, J. Bacteriol. 54:549 (1947).

(MTCC=Microbial type culture collection, Institute of Microbial Technology, Chandigarh, India)

Example 6

The working of the system was characterized in details using different concentrations of mycolic acid. Different concentrations (100, 250, 500, 1000 µg/ml) of mycolic acid were allowed to form complexes with the stain as described in the previous sections and the increases in absorbance patterns were recorded indicating the increases in the intensity of the colour (FIG. 4).

Example 7

By using this method the mycolic acid produced by the control was quantified as well as treated cells of *M. smegmatis* with different plant extracts and compounds. Some of the compounds are known to inhibit mycolic acid biosynthesis and others are plant extracts and unknown compounds. The compounds and the extracts were selected on the basis of loosening of acid fast stain in *Mycobacterium smegmatis*.

The culture of *Mycobacterium smegmatis* was frown in nutrient broth containing the sub-lethal concentration (½ MIC) of the compounds/extracts for 48 hrs. The cells were harvested by centrifugation and the pellets were lyophilized. Equal amount of the cells (100 mg) were taken both of control and treated cells and kept for methanolysis overnight as described in Example 1. The extracted hexane layer was allowed to dry and a common stock (5 mg/ml) was used to run a TLC plate to determine how much the inhibition of mycolic acid by calculation the amount of produced mycolic acid by a densitometer.

Compounds, which were showing loosening of acid fast staining, were also tested for spectrophotometric assay. The strain of *Mycobacterium smegmatis* giving 100% acid fast staining was grown for 48 hours in 50 ml culture media. As described earlier treatment of different compounds were given at sub-lethal concentrations in replicates were also grown for 48 hours. The control along with different treated cells were pelleted by centrifugation and lyophilized to get the dry pellet of the cells. Equal weight (100 mg) of the cells (control as well as treated) were kept for methanolysis overnight. After 18 hrs. incubation the hexane fraction was extracted and dried. A common stock (5 µg/ml) was made for the control as well as treated cells by using hexane as a solvent. Equal amounts (v/v) of carbol fuchsin dye was added and mixed properly, and the upper hexane layer which was transparent initially, turned into a pink colour whereas in the case of treated cells the intensity of the pink colour was less than the control cells.

The details of the treatments and the absorbance by different treatments are described in Table 2.

TABLE 2

| Compounds/extracts | Concentration of the compound/ extract for treatment | Stock used to take the absorbance | absorbance at 495.89 nm |
|---|---|---|---|
| *Catharanthus roseus* root extract in ethanol | 312 µg/ml | 5 mg/ml | 0 |
| Thebaine | 150 µg/ml | 5 µg/ml | 0 |
| Isoniazid | 1 µg/ml | 5 µg/ml | 0 |
| Control | — | 5 µg/ml | 1.4885 |

Isoniazid is a known mycolic acid biosynthesis inhibitor which when treated with *Mycobacterium smegmatis* does not allow the production of mycolic acid. Similarly the other plant-based compounds thebaine and extracts like "*Catharanthus roseus* root ethanolic extract" do not allow the synthesis of mycolic acid. So this method can be used to screen the synthetic, semi-synthetic or natural compounds and the extracts may be from a prokaryotic or an eukaryotic source. Similarly, the mycolic acid biosynthesis inhibition can be checked not only for mycobacteria but also in other groups like *Corynebacterium* and *Nocardia*.

The person skilled in the art may use different species of mycolic acid and different dye complexing with mycolic acid producing different absorption maximas but the essence of the invention is that any dye complexing with different species of mycolic acid and producing different absorption maxima can be assayed at that wavelength if the optical density at that maxima vary proportionately with the concentrations.

The above illustrations in the examples describe in detail the use of an already-invented procedure to devise a novel, quick and low cost system of screening potential inhibitors of mycolic acid biosynthesis. This system may look simple but has tremendous importance and potential as millions of compounds and extracts are to be screened to arrive in a potential non-toxic drug formulation. The commercial potential of the invention may also be exploited in form of a kit to detect mycolic acid that will have an immediate impact in detection of mycobacterium.

What is claimed is:
1. A method of screening mycolic acid biosynthesis inhibitors useful as anti-microbial agents by quantifying the amount of mycolic acid produced by bacteria in the presence and absence of a test compound or extract, said method comprising:
   a. growing separate cultures of the said bacteria in the presence and absence of said test compound or extract for time duration ranging between 40–60 hours,
   b. lyophilizing each culture to obtain a bacterial pellet,
   c. extracting mycolic acid from the pellet, d. dissolving extracted mycolic acid obtained from each pellet in hexane to obtain mycolic acid solution, e. adding said solution to carbol-fuschin dye in the ratio ranging between 1:4 to 4:1 (v/v), f. shaking the product of step (e) vigorously to obtain a pink color mycolic acid-dye complex as an upper layer, g. quantifying said mycolic acid spectrophotometrically at a wavelength ranging between 490–500 nm, and h. determining degree of inhibition of mycolic acid biosynthesis in the test compound treated bacterial culture.

2. A method as claimed in claim 1, wherein quantifying the amount of mycolic acid is accomplished spectrophotometrically at a wavelength ranging between 494–496 nanometers.

3. A method as claimed in claim 1, wherein the ratio of carbol Fuchsin dye to said mycolic acid solution is in the ratio 1:1 (v/v).

4. A method as claimed in claim 1, wherein the carbol fuchsin consists of basic fuchsin dye in the concentration ranging between 0.1–1.0 gm/100 ml, phenol, 95% ethanol, and distilled water, said constituents in the ratio:

(i) phenol:ethanol in ratio ranging between 1:4 to 2:1 (v/v), and ii) phenol:distilled water in the ratio ranging between 1:14 to 1:25 (v/v).

5. A method as claimed in claim 1, wherein said test compound or extract with inhibitory activity is added at concentrations ranging between 1/25 to 1/2 of minimum inhibitory concentration (MIC).

6. A method as claimed in claim 1, wherein said antimicrobial agents are developed against microbes comprising Mycobacterium, Corynebacterium, and Nocardia.

7. A method as claimed in claim 1, wherein said method is used to screen for inhibitors selected from the group consisting of synthetic, semi-synthetic, natural compounds, and extracts.

8. A method as claimed in claim 1, wherein the intensity of color increases with an increase in the concentration of mycolic acid.

9. A diagnostic kit for identifying potential anti-microbial drugs against mycolic acid producing microbes, said kit comprising carbol fuchsin, methanol, toluene, hexane and concentrated sulphuric acid, with said constituents in the following ratios:

(i) methanol:toluene ranging between 1:3 to 3:1 (v/v), (ii) methanol:hexane ranging between 2:1 to 8:1 (v/v), (iii) concentrated sulphuric acid:hexane ranging between 1:2 to 1:8 (v/v), and (iv) Carbol fuchsin:hexane ranging between 1:4 to 4:1 (v/v).

10. The kit as claimed in claim 9, wherein the carbol fuchsin consists of basic fuchsin dye in the concentration ranging between 0.1–1.0 gm/100 ml, phenol, 95% ethanol, and distilled water, said constituents in the ratio:

(i) phenol:ethanol in ratio ranging between 1:4 to 2:1 (v/v), and (ii) phenol:distilled water in the ratio ranging between 1:14 to 1:25 (v/v).

11. The kit as claimed in claim 9, wherein the bacteria comprising said bacterial pellet is selected from group consisting of Mycobacterium, Corynebacterium, and Nocardia.

12. The kit as claimed in claim 9, wherein said test compound or extract with inhibitory activity is added at concentrations ranging between 1/25 to 1/2 of minimum inhibitory concentration (MIC).

* * * * *

UNITED STATES PATENT AND TRADEMARK OFFICE
CERTIFICATE OF CORRECTION

| | |
|---|---|
| PATENT NO. | : 6,833,249 B2 |
| APPLICATION NO. | : 10/102939 |
| DATED | : December 21, 2004 |
| INVENTOR(S) | : Khanuja et al. |

It is certified that error appears in the above-identified patent and that said Letters Patent is hereby corrected as shown below:

On the title page: Item (75) (Inventors) please add the following:

--Mahendra Pandurang Darokar, Uttar Pradesh (IN); Soumya Awasthi, Uttar Pradesh (IN)--

Signed and Sealed this

Twenty-fourth Day of April, 2007

JON W. DUDAS
*Director of the United States Patent and Trademark Office*